United States Patent
Kloster et al.

(10) Patent No.: US 9,145,871 B2
(45) Date of Patent: Sep. 29, 2015

(54) V-SPRING CONFIGURATION AND END ATTACHMENT ASSEMBLIES THEREFOR FOR USE IN A PERSONAL CARE APPLIANCE

(71) Applicant: KONINKLIJKE PHILIPS N.V., Eindhoven (NL)

(72) Inventors: Tyler G. Kloster, Snoqualmie, WA (US); Hendrik Richard Jousma, Groningen (NL); Michiel Allan Aurelius Schallig, Drachten (NL); Martinus Bernardus Stapelbroek, Frieschiepalen (NL); Patrick A. Headstrom, Seattle, WA (US); Scott E. Hall, Issaquah, WA (US); Wolter F. Benning, Seattle, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 27 days.

(21) Appl. No.: 14/073,943

(22) Filed: Nov. 7, 2013

(65) Prior Publication Data

US 2014/0060975 A1 Mar. 6, 2014

Related U.S. Application Data

(62) Division of application No. 13/000,746, filed as application No. PCT/IB2008/052666 on Jul. 2, 2008, now abandoned.

(51) Int. Cl.
*F16F 1/14* (2006.01)
*F03G 1/02* (2006.01)
*A61C 17/34* (2006.01)
*F16F 1/02* (2006.01)

(52) U.S. Cl.
CPC .............. *F03G 1/02* (2013.01); *A61C 17/3418* (2013.01); *F16F 1/025* (2013.01); *A46B 2200/1066* (2013.01); *Y10T 403/7062* (2015.01)

(58) Field of Classification Search
USPC .......................... 267/160, 180; 15/22.1, 167.1
See application file for complete search history.

(56) References Cited

U.S. PATENT DOCUMENTS 8,413,969 B2 * 4/2013 De Jong et al. ............... 267/180
2003/0115693 A1 6/2003 Grez et al.

(Continued)

FOREIGN PATENT DOCUMENTS

WO 2008001302 A2 1/2008
WO WO 2008/001302 * 1/2008

*Primary Examiner* — Christopher Schwartz (57) ABSTRACT

A V-spring member (18) for use in a driving system for a personal care appliance has regions (34, 36) at the ends of the spring which are large enough to support a contact with an end clamping assembly, the spring member including a crosspiece (40) extending between the longitudinal edges of the spring at the end regions, such that the ends of the spring member define a closed line. End clamping assemblies (16, 24) provided for such a V-spring member include a body portion (64) having a lower support portion (66) on which the V-spring is supported and a mating clamping member (88) positioned in registry with the support portion on top of the V-spring. The support portion and the clamping member include peripheral edges (74, 92) which have a curved cross-sectional configuration, and which are in registry, making contact with the spring member in the end regions in such a manner as to reduce stress concentrations in the end regions of the spring, thereby reducing fretting fatigue and fretting damage in the spring.

16 Claims, 7 Drawing Sheets

(56) References Cited

U.S. PATENT DOCUMENTS

| | | |
|---|---|---|
| 2003/0204924 A1 | 11/2003 | Grez et al. |
| 2005/0177962 A1 | 8/2005 | Chan |
| 2011/0119848 A1* | 5/2011 | Kloster et al. ............... 15/167.1 |
| 2012/0326370 A1* | 12/2012 | Kloster et al. ................ 267/154 |
| 2014/0300039 A1* | 10/2014 | De Jong et al. ............... 267/154 |

* cited by examiner

V-SPRING CONFIGURATION AND END ATTACHMENT ASSEMBLIES THEREFOR FOR USE IN A PERSONAL CARE APPLIANCE

CROSS REFERENCE TO RELATED CASES

This application is a divisional of co-pending U.S. patent application Ser. No. 13/000,746, filed Dec. 22, 2010 which is a U.S National Stage Application under 35 U.S.C. §371 of International Application No. PCT/IB2008/052666, filed Jul. 2, 2008 and U.S. Provisional Ser. No. 60/874,839, filed Dec. 13, 2006.

This invention relates to the configuration of a V-spring member used in a drive assembly for a personal care appliance and also concerns end attachment assemblies for the V-spring. Both the V-spring and the end attachment assemblies designed to reduce fatigue and wear during operation thereof.

Many personal care appliances, such as power toothbrushes, but other devices as well, for example, shavers and similar devices, use a spring assembly which is clamped at both ends as part of their driving assembly. Different spring configurations are used, including a V-shaped solid spring. In some arrangements, the spring is part of a nodal-mounted drive system. Different spring configurations are used, including a V-shaped solid spring. In operation, however, spring arrangements, including the V-spring arrangement, are subject to fatigue and wear, generally referred to as fretting, resulting in failure due to fretting fatigue, where high stresses are created by shear and normal forces in the interface structure at the clamped ends of the spring, as well as fretting damage due to relative motion between the parts, which eventually damages the parts sufficiently to produce a failure.

More particularly, fretting fatigue results when high surface pressures on an individual part, such as a V-spring, are present along with high shear forces. Surface pressure on the spring is caused by deformation in the surface of the material caused by attachment elements, such as a clamp. While surface deformation is typically very small, it can still cause very high local pressure areas, particularly when shear forces are present. Fretting damage results when the ends of the V-spring and the end attachment assemblies move relative to each other during normal twisting operation of the spring.

Hence, it is important that the configuration of the V-spring and the arrangement of the end attachment assemblies at the ends of the V-spring are designed to minimize fretting fatigue and fretting damage on the V-spring so that the appliance can operate for its expected lifetime.

Accordingly, one embodiment disclosed herein is a V-spring member for use in a driving system for a personal care appliance, comprising: an elongated solid spring member, having a cross-sectional configuration in the form of a V, wherein the spring member has regions at the ends thereof which are large enough to support a contact from an end clamping assembly, the spring member further including a cross-piece extending between the longitudinal edges of the spring member in the end regions thereof, such that the ends of the spring member define a closed loop.

Another embodiment is an end assembly for clamping an end of an elongated solid V-spring drive member used in a personal care appliance, comprising: an end block member having a lower support portion on which an end region of the V-spring is positioned, wherein the lower support portion includes an upper peripheral edge which in cross-section is curved to contact an inner surface of the V-spring in an end region thereof; and a clamping member which is positioned on top of the V-V-spring for clamping the end region of the V-spring to the lower support portion of the end block member, the clamping member having a lower surface configuration which fits over the V-spring, the clamping member including a peripheral edge, curved in cross-section, which contacts an outer surface of the V-spring substantially in registry with the lower support portion at the inner surface of the V-spring, wherein the physical contact between the lower support portion and the clamping member, respectively, and the V-spring, including the shape of the respective peripheral edges, results in reduced stress concentrations with the V-spring, thereby reducing fretting damage and fretting fatigue.

In other embodiments, the spring member is glued to, or welded/brazed to the end assemblies.

Figure 1:
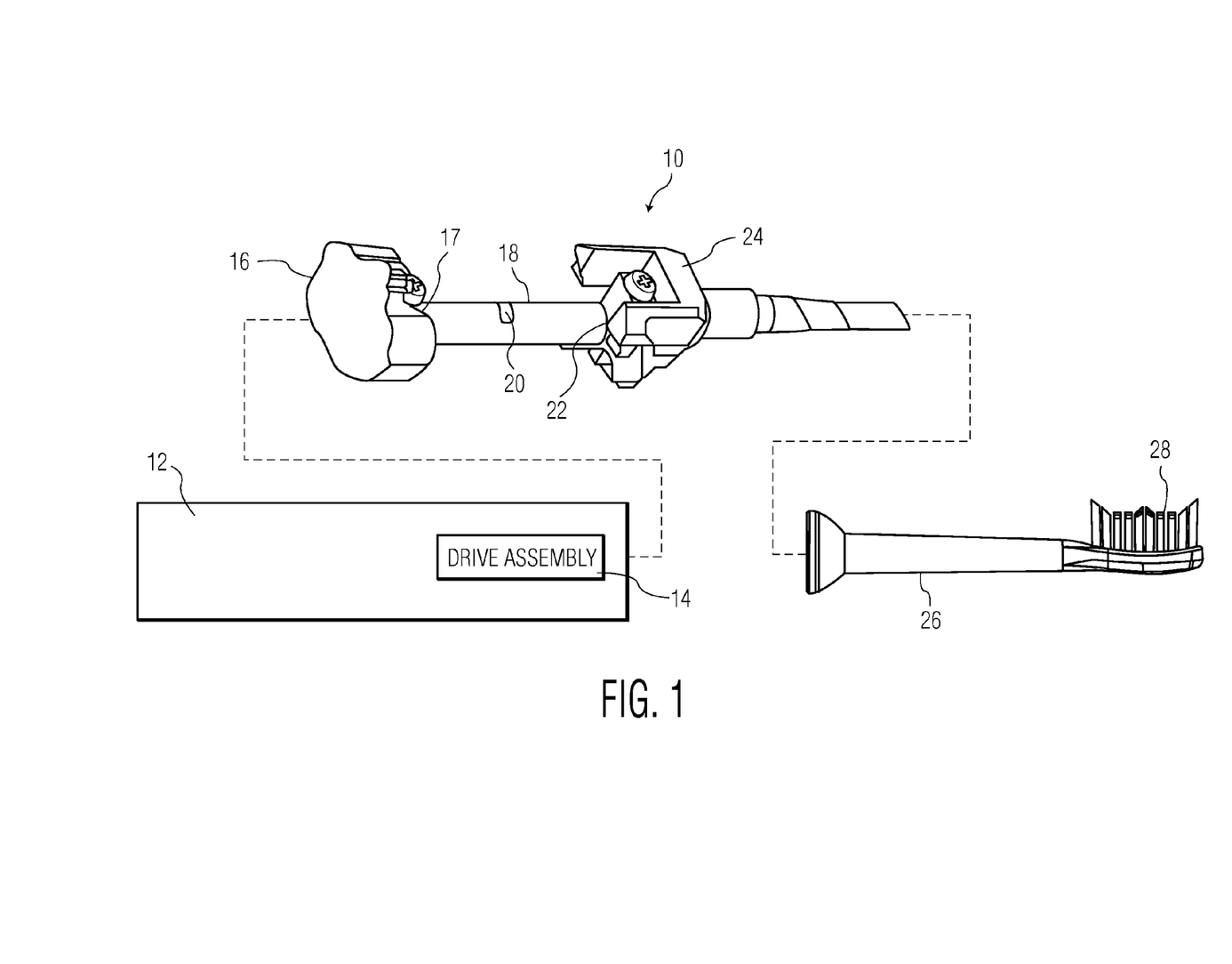
FIG. 1 is an exploded view of a personal care appliance (toothbrush) incorporating a V-spring and end attachment assemblies.

FIG. 1 shows a personal care appliance, in particular, a power toothbrush 10. Power toothbrush 10 includes a handle assembly 12 in which is positioned an illustrative drive assembly 14. The drive assembly may have various configurations and arrangements, including a motor with drive shaft, an electromagnetic arrangement, or other similar electrical/mechanical arrangements. In FIG. 1, drive assembly 14 drives a drive hub assembly 16 through an oscillating back-and-forth action. This oscillating action may have various configurations/paths of travel. One example is a partial rotational action through an angle of 16° (±8°). Other actions include a vibrating back-and-forth action, as well as more complex actions.

Connected to and extending from drive hub assembly 16 is a proximal end 17 of a V-spring 18. In some arrangements, V-spring 18 will be nodally mounted, i.e. center point 20 along the V-spring will function as a node point and thus will not move while the opposing end portions of the V-spring counter-rotate. The nodal-mounted arrangement is not necessary to the invention, however. The distal end 22 of the V-spring is mounted in a workpiece hub assembly 24; in this case, a brush hub assembly, connected to a mounting arm 26 on which is mounted a toothbrush brush element 28. The V-spring may be used in other personal care appliances.

In one embodiment, V-spring 18 is 1.38 inches long, with the two side wall portions being 0.16 inches wide and 0.012 inches thick. The V-spring is made from stainless steel and includes three openings along the peak of the V-spring one at either end to accommodate bolts for clamping the V-spring in a particular assembly and another at the center to accommodate a bolt for a nodal attachment member. The angle between the two longitudinal walls of the V-spring is approximately 90° in the embodiment shown, although this can be varied, e.g. within a range of 45°-170°.

V-spring 18 is configured particularly to reduce stress concentrations in the end regions of the spring, thereby reducing both fretting fatigue and fretting damage in the spring. As discussed above, fretting fatigue occurs when high surface pressures are present along with high shear forces, while fretting damage occurs when two surfaces, such as the end regions of the spring and the end attachment assemblies move relative to each other in operation of the appliance. The V-spring of the present embodiment is designed to permit a transition within the spring at the end regions thereof, from the relatively soft or elastic rotational movement of the center area of the spring to the hard, rigid (stiff) hub assemblies at the ends thereof. Specifically, the spring is designed such that in the end regions there is substantially no tension deformation during operation of the appliance.

In one arrangement, shown in FIG. 2A, the V-spring includes two extended end regions 34 and 36, which extend below the longitudinal edges 37 of the middle portion of the V-spring. The width of the end regions may vary, but must be wide enough to accommodate the size and configuration of the portion of the end attachment assemblies which contact the spring. As one example, the width of these extended end regions could be within the range of 2-7 mm. Further in one embodiment, the extended regions extend below the longitudinal edge 37 by approximately 2 mm. The free ends of the extended portions are joined by a flat cross-piece 40 which has the same width as the extended end regions 34 and 36.

Preferably, the cross-piece 40 is integral, i.e. unitary, with the remainder of the spring, with the ends of the extended regions of the spring and the cross-piece having curved joints 41 for a smooth transition, referred to as closed end regions. This "closed end" region is present at both ends of the V-spring. The cross-piece could also, however, be a separate piece of material, attached by welding or other means, for some applications.

Figure 2A:
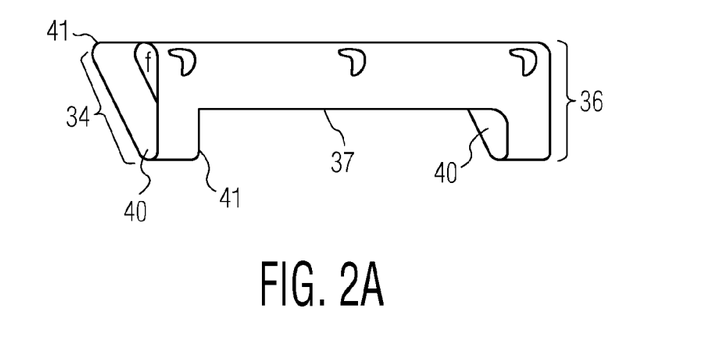
FIGS. 2A-2B show two V-springs with different end regions.
Figure 2B:
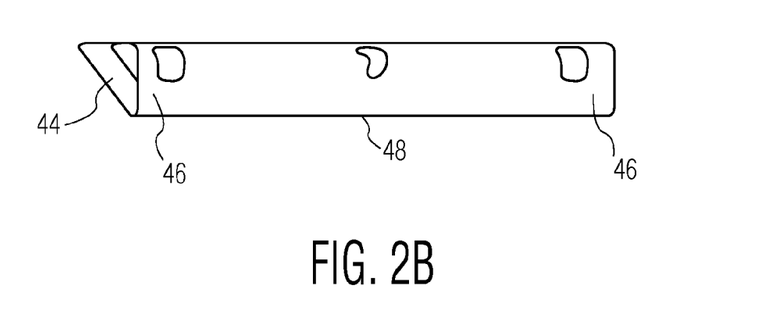

As a variation of the arrangement of FIG. 2A, shown in FIG. 2B, the end regions 46 have edges which are simply extensions of edges 48 of the middle portion of the spring. The cross-piece 44 has a specific width which defines the end regions of the spring. Again, preferably, the cross-piece is integral, i.e. part of the same piece of material, with the remainder of the V-spring. Alternatively, however, in some applications, the cross-piece 44 could be a separate piece but attached to the V-spring, such as by welding or some other secure attachment.

The closed end arrangement has a configuration which permits attachment of the spring to the end assemblies in end regions which have very high rotational stiffness compared to the rotational stiffness of the remainder (the middle portion) of the V-spring. The end regions, because of their stiffness, experience relatively little strain, when the spring is connected to the end assemblies in these regions. This permits end attachment assemblies, when properly designed, as discussed in detail below, to hold the spring in such a manner as to provide a stress transition area within the spring between the softer rotational (middle) portion of the spring and the hard, rigid (stiff) hub members.

As a further modification of the closed end configuration, the entire end area (the area defined by the end edges of the spring and the edge of the cross-piece) could be a plate element either integral with the spring or added to it, by welding or other secure attachment means.

The closed end V-spring arrangement (FIGS. 2A, 2B) is advantageous, since it makes possible stress transitions within the spring itself, when used in combination with end attachment assemblies having an effective configuration, discussed below. This combination results in a reduction of the fretting fatigue and damage, allowing the appliance to operate for a normal life time.

In addition, such an arrangement reduces or eliminates micromotion and hence damping, resulting in a higher linearity and Q, as well as making certain simulations easier. While the figures show the V-spring being held at both ends, it is possible that only one connection may be used in a particular application. In other applications, more than two connections may be used.

Figure 3:
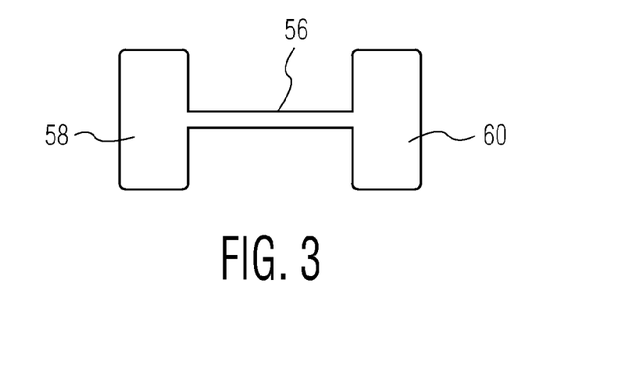
FIG. 3 is a simplified elevational view showing a wire spring alternative to the V-spring of FIG. 1.

Another example of the basic concept discussed above is shown in FIG. 3, which includes a wire spring 56, other than a V-spring configuration, having two enlarged end elements 58 and 60. In one specific example, wire spring 56 could be 1.0 mm in diameter by 50 mm long, with the end elements 58 and 60 being of such as size and arrangement that they are significantly stiffer, e.g. five times stiffer, than the wire spring 56. In order to achieve such a stiffness, the end elements could be 5 mm wide with a commensurate diameter of approximately 16 mm. The end elements 58 and 60 provide the desired transition zone between the soft rotational action of the wire spring 56 and the stiff hub attachment assemblies, which connect to the other portions (drive side and workpiece side) of the appliance.

FIGS. 4-11 are directed toward hub attachment assemblies for springs, particularly for V-springs, to reduce the fretting. In order to achieve the desired reduction in fretting fatigue and/or fretting damage, the hub attachment assemblies must be configured to significantly reduce the stress concentrations in the connecting/transition regions of the spring.

Figure 4:
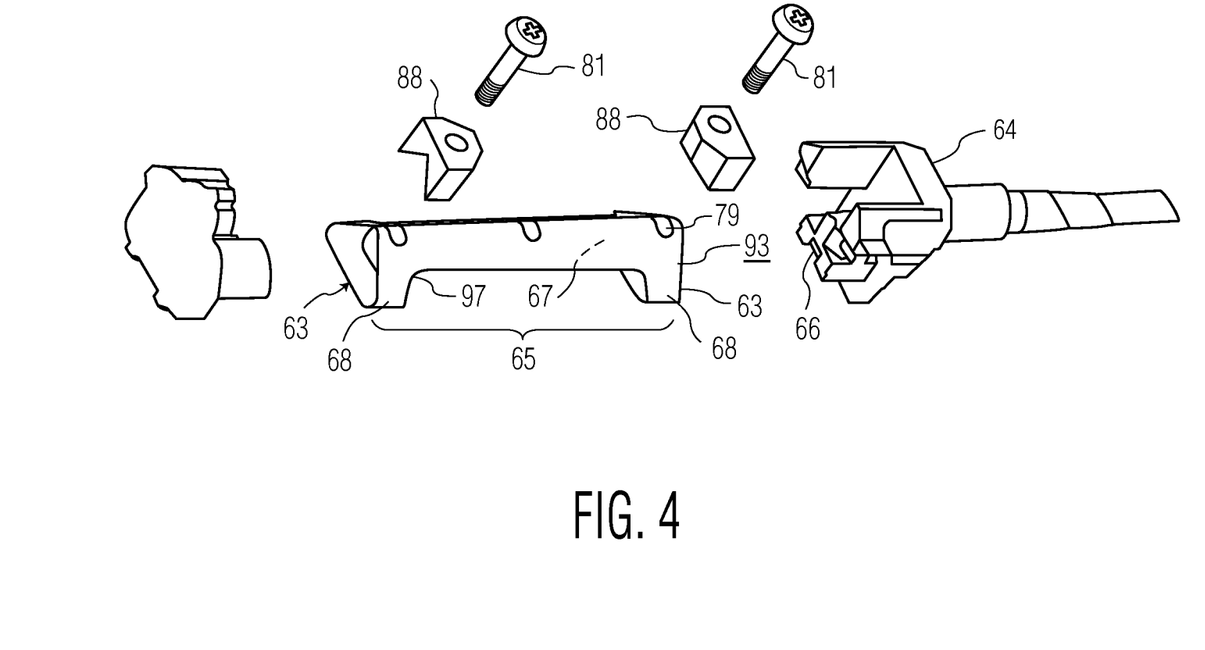
FIG. 4 is an exploded view showing the V-spring and the end attachment assemblies for a closed end V-spring.

A first arrangement, shown in FIG. 4, is for a closed end V-spring, using a clamp-type hub attachment assembly. The hub attachment assembly includes a body portion 64 with an integral spring support portion 66. Body portion 64 receives driving action from a driving assembly when it is part of the driving hub attachment assembly, or drives a mounting arm for a workpiece when it is part of a workpiece hub attachment assembly. The configuration of the spring support portion 66 is important to proper operation of the hub attachment assembly to accomplish reduction of fretting, and is shown in detail in FIG. 5 as well as in FIG. 4.

Figure 5:
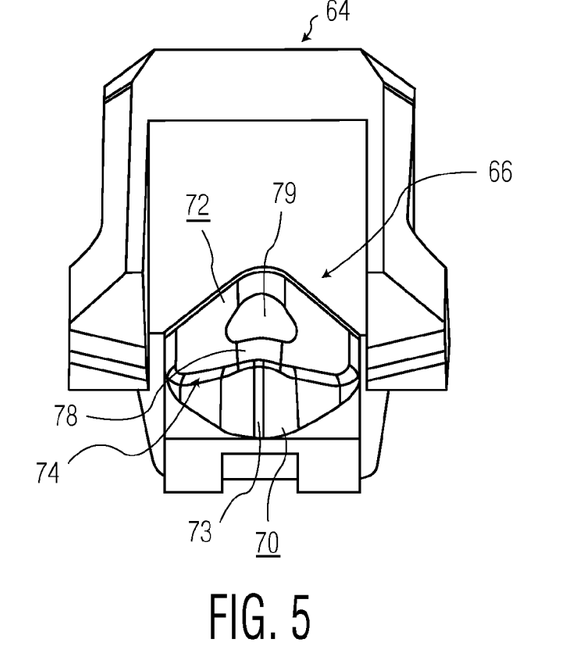
FIG. 5 is an elevational view showing an end assembly with a support portion.

The closed end 63 of V-spring 65 in FIG. 4 is fitted over the spring support portion 66, as shown in FIG. 4. Referring to FIG. 5 in particular, the spring support portion 66 includes a vertical surface 70, and an upper longitudinally extending surface 72 which generally parallels the longitudinal direction of the V-spring 65. Portions of longitudinal surface 72 of spring support portion 66 make physical contact with inner surface 67 of the V-spring, in the end regions 68 of the V-spring, which in FIG. 4 include extended portions.

Vertical surface 70 curves away from body portion 64 to center area 73 and then back again to the body portion. The vertical surface 70 can be smoothly curved, or it can be in the form of a series of flat portions angled successively relative to each other to form a substantially curved surface, as shown in FIG. 5.

The longitudinal surface 72 is in the form of an inverted V with a shallow curved portion 78 at its highest point, which extends for the length (from the front to the rear, adjacent the body portion) of the spring support portion. Approximately in the center of the shallow curved portion 78 is an opening 79 to receive a clamping bolt 81. The opening 79 can be threaded or not, in which case the bolt 81 is secured by a nut (not shown) located beneath the spring support portion.

The remainder of the longitudinal surface 72 on either side of the shallow curved portion 78 has a complex and subtle configuration. The peripheral edge 74 of longitudinal surface 72 has a shallow curve in cross-section. This curved peripheral edge 74 is the line of contact between spring support portion 66 and the inner surface of the V-spring. The edge 74 has a sufficiently shallow curved cross-section, as opposed to a sharp edge, to produce an effective and efficient transfer of load between the respective hub attachment assembly and the spring, while reducing stress concentrations in the spring itself. The geometry of the peripheral edge 74, which extends all the way around longitudinal surface 72, has a radius which allows the spring to deform naturally as it rotates back and forth in normal operation, minimizing high contact stresses between the end portions of the spring and the hub attachment assemblies, which create fretting fatigue and failures. The longitudinal surface 72 inboard of the curved peripheral edge 74 extends downwardly/inwardly away from edge 74 so that only the peripheral edge 74 makes physical contact with the spring.

Each hub attachment assembly also includes a clamping member 88 (FIG. 6) which has surfaces which are substantially similar to or mirror images of the spring support portion 66, in order to provide a good clamping action. Clamping member 88 includes an opening 90 which is either threaded or not to threadably receive a bolt 81 or permit bolt 81 to mate with a nut positioned beneath spring support member 66. The bolt 81 is tightened sufficiently to hold the spring end regions so as to reliably result in a transfer of force between the hub attachment assemblies and the spring, either into the spring from a drive assembly or from the spring to the workpiece, but not tightened so hard as to cause deformation of the spring in the regions of contact between the clamping member and the spring support member portion, respectively, against the spring.

Figure 6:
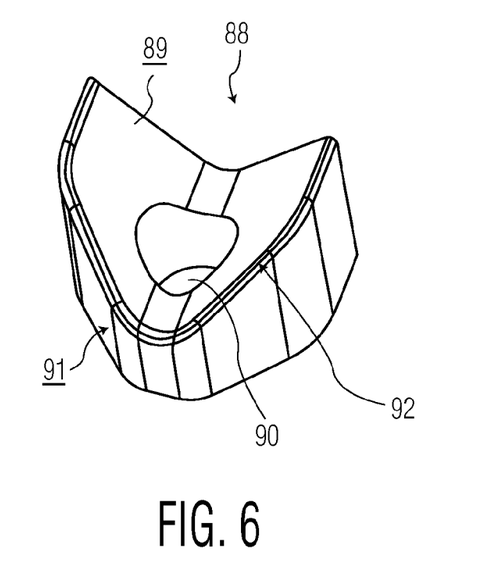
FIG. 6 is a perspective view showing an end assembly clamping member.

In more detail, the longitudinal surface 89 of the clamping member 88, i.e. the lower surface thereof when operatively positioned against a spring, includes a peripheral edge 92 which has the same cross-sectional curve or radius as edge 74 in the spring support member 66. Peripheral edge 92 makes contact between clamping member 88 and the outer surface 93 of the spring member in the end regions thereof. The remainder of the longitudinal surface 89 inboard of edge 92 extends slightly inwardly away from the peripheral edge 92 so as not to make additional contact with the spring member. Only the curved surface of the peripheral edge 92 makes contact with the spring. The surface 91 of the clamping member also generally matches the vertical surface 90 configuration of spring support portion 66.

The longitudinal V-shaped surfaces of both the spring support member and the clamping member are thus arranged to generally fit the end regions of the spring, i.e. those relatively stiff regions of the spring relative to the remainder of the V-spring. The specific V angle of the spring support member and the clamping member are discussed below for one embodiment.

The contact between the spring support portion 66, clamping member 88 and the inner and outer surfaces of the end regions of the V-spring is an important consideration in reducing fretting fatigue and failures. The clamping member 88 secures the end regions of the spring to the spring support portion 66 by a bolt in one embodiment, as discussed above. Other embodiments could include a rivet or other attachment means. The curved peripheral edges 74 and 92 of the spring support member 66 and the clamping member 88, respectively, are important for minimizing stress concentrations between the spring and the hub attachment assemblies. The area of contact between the hub attachment assemblies and the V-spring is within the end regions of the spring, where the spring deflection is transitioned to the hub assemblies.

Figure 7:
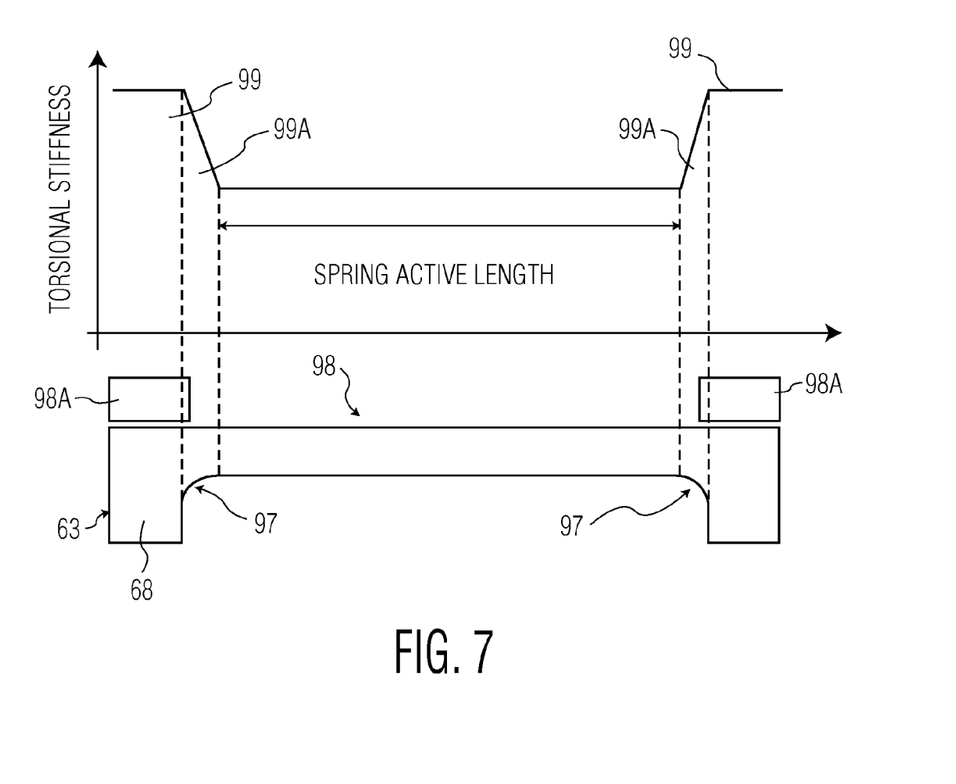
FIG. 7 is a diagram showing stiffness transition along a closed end V-spring.

FIG. 7 shows a stiffness transition diagram for a closed end spring. The clamping area is physically away from high stress regions of the spring, i.e. the inside corners of spring 97 in FIG. 7, and is maintained within the static zone of the spring, i.e. within the end region areas. The spring is shown at 98 and the clamping members at 98A. The safe clamping zones are shown at 99 while the stiffness transition zone within the spring is shown at 99A.

The V-angle of spring support portion 66 and clamping member 88 is close to or equal to the bend angle of the spring. Variations in the V-angles of the clamping member and the spring support member relative to the angle of the spring can be accommodated, although residual stresses may vary depending on the particular angular mismatch. Typically, it is desirable that the angle of the clamping member 88 be slightly less than the angle of the V-spring, and the angle of the spring support member 66 be slightly greater than the angle of the spring. The angular differences are such that application of clamping pressure will bring the three pieces together. Having the clamping member with a greater angle than the spring and the spring a greater angle than the spring support member would result in an undesirable contact between the V-spring and the spring support member when the three pieces are clamped together.

With the above arrangement, the hub attachment assembly is constrained in all six degrees of freedom by the contact between the hub attachment assembly (the spring support portion thereof), the clamping member and the V-shaped spring. X and Z translations are constrained by the actual surface contacts of the three members, while Y translation is constrained primarily by friction between the several contact surfaces. X axis rotation is constrained by the surface contact distributed along the outer and inner surfaces of the spring, while Y axis rotation is constrained by the surface contact between the spring and the clamping member, and Z axis rotation is constrained by the surface contact between the outer and inner surfaces of the spring and either the peripheral edge of the spring support contact of the hub attachment assembly or the surface contact on the opposing side of the spring.

The clamping force created by the bolt allows the entire assembly to efficiently transfer loads from the drive hub attachment assembly to the spring and from the spring to the workpiece hub attachment assembly. It is important that the clamping force created by the bolt be large enough that there is no gap between the spring and the clamping member. This is important so that the torque is reacted by the clamping member on one side of the spring and the spring support member on the other side.

Another significant feature of the hub attachment assembly structure involves the selection of material, in particular the material for the spring support portion 66 and the clamping member 88. The material should be such as to minimize high contact stresses at the interface between the clamping areas of the hub attachment assembly and the V-spring in the end regions of the V-springs. The material of both the spring support portion and the clamping member should be no harder than the material comprising the spring in the closed end arrangement.

With a steel V-spring, for instance, the spring support portion 66 at the drive hub attachment assembly can be made from steel or a softer material, while at the workpiece hub attachment assembly the spring support portion can be made from zinc, which is softer than the steel V-spring and will not result in fretting of the spring even if there is some relative motion between the parts. It will also reduce fretting fatigue stresses by lowering the contact pressures and the resulting shear forces between the parts produced by operation of the appliance.

Aluminum clamp blocks, which is a softer material than the steel V-spring, can be used at both the drive hub attachment assembly and at the workpiece hub attachment assembly. The aluminum provides good fretting resistance and is stiff enough to make the clamped assembly sufficiently rigid to transfer the torque forces along the appliance.

Figure 8:
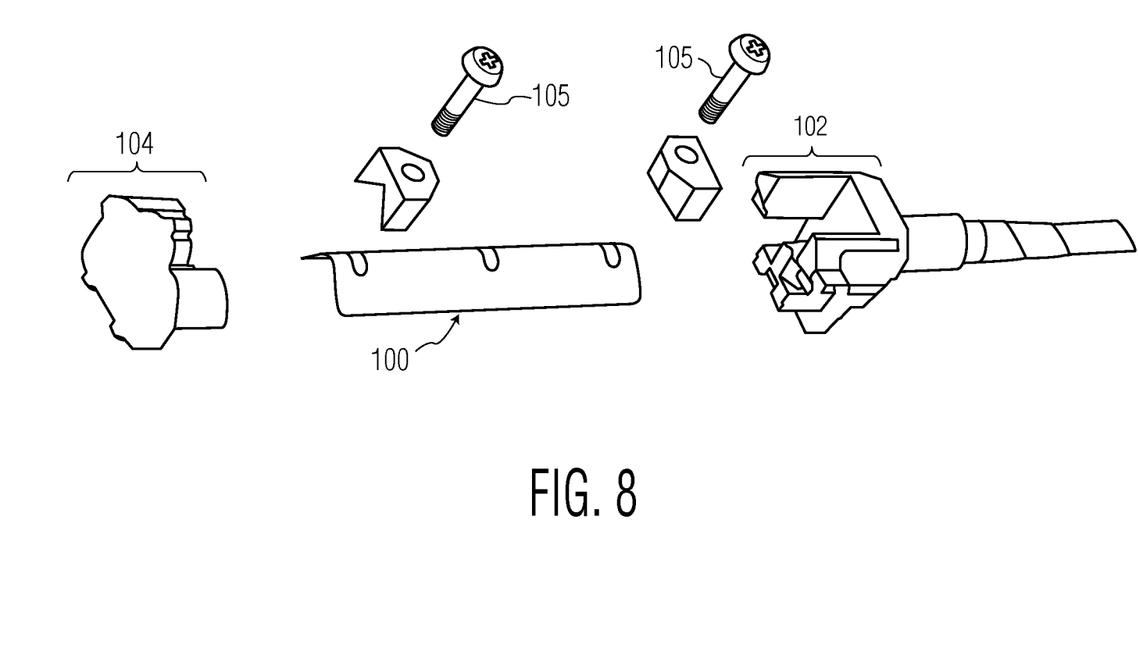
FIG. 8 is an exploded view showing a V-spring with end attachment assemblies for an open end V-spring.

FIG. 8 shows an embodiment in which the V-spring has an open ended configuration. The V-spring is shown at 100 with a drive hub attachment assembly 102 and a workpiece hub attachment assembly 104. Spring 100 has a V configuration from end to end with no cross-pieces or extended portions at the ends thereof. The drive hub attachment assembly and the workpiece hub attachment assembly are substantially identical to that shown and described relative to FIGS. 4 and 5, i.e. both hub attachment assemblies have spring support portions integral therewith which contact the inner surface of the V-spring in end regions thereof. The hub attachment assemblies also include clamping members 105 which clamp the spring to the spring support portions by a threaded bolt/nut, or similar attachment means, the clamping members having the same configuration and arrangement as shown in FIG. 6.

In the open-ended spring arrangement, however, the spring support portions are zinc for both the drive hub attachment assembly and the workpiece hub attachment assembly. Zinc provides the most resistance to fretting for an open spring arrangement. In addition, aluminum clamping members are used for both hub attachment assemblies.

The relative geometries of the spring support member and the clamping member are the same for the open-ended V-spring arrangement as for the closed end V-spring arrangement. Stresses provided by the hub attachment assemblies are, however, located in the center of the end regions of the spring, as opposed to the edges thereof for the closed end arrangement. This reduces the requirement for spring edge quality. Consistent clamping is important in minimizing spring rate variation in the open-ended arrangement.

Figure 9:
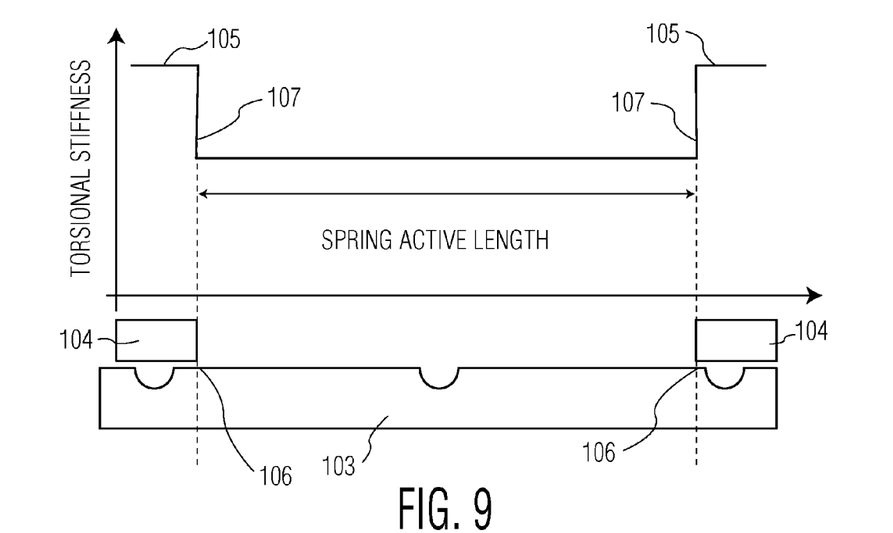
FIG. 9 is a diagram showing stiffness transition along an open end V-spring.

FIG. 9 shows a stiffness transition diagram for the open-end V-spring 103, with clamping members 104. The clamping zones are shown at 105. The stiffness transition occurs at the clamping location 106. In the open-end embodiment, a rapid change in stiffness creates a stress riser, shown at 107, within the spring.

Figure 10:
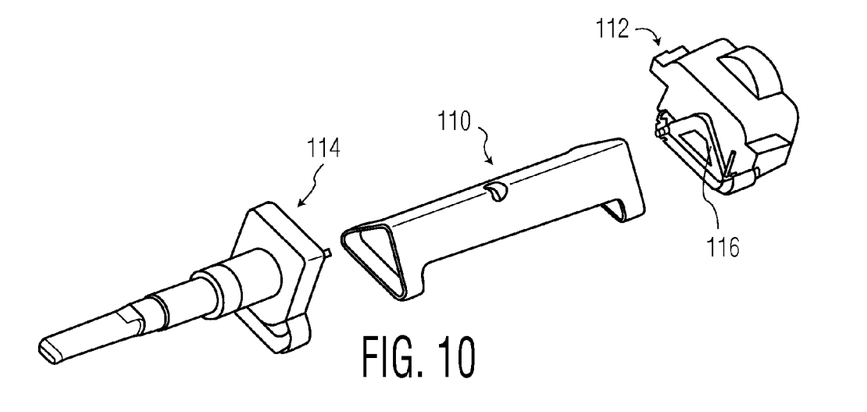
FIG. 10 is an exploded view showing a closed end V-spring with glued-in end assemblies.

A further embodiment is shown in FIG. 10. In this embodiment, a closed end V-spring 110 is glued into steel end attachment assemblies 112 and 114. Each end attachment assembly includes a generally triangular slot 116 which is configured to receive the end regions of the closed V-springs. The slot is filled with an adhesive, such that the end regions of the V-spring are stiffly glued to the end attachment assemblies. Typically, the depth of the slot will be approximately 2 mm.

In operation, the adhesion between the glue and the surface of the spring in the end regions will eliminate relative motion between the spring and the end attachment assemblies and will hence significantly reduce fretting damage. The adhesive creates a continuous interface around the entire closed end of the spring which will reduce contact stresses and stress concentrations due to hard points of contact. The robustness of the glue is important for the proper operation of this embodiment. The adhesive will constrain the parts in all six degrees of freedom during operation of the appliance. Further, the adhesive interface provides the primary load transfer capability between the hub attachment assemblies and the V-spring.

In this embodiment, the adhesive used is a dual-cure (UV and moisture) adhesive. The spring is located by contact elements within the slot 116, which holds the spring in a selected relationship relative to the end attachment assembly. After the adhesive is positioned in the slot and after the glue has cured, the interface between the hub attachment assemblies and the V-spring is sufficiently rigid for proper operation of the appliance. In operation, the primary torque is created by the acceleration of the hub attachment assemblies through their normal rotational amplitude. The torque is then reacted by the surface forces of the adhesive-to-spring interface. This arrangement provides reliable reactive force between the spring and the hub attachment assemblies and vice versa. Because there is little or no relative motion of the parts, and little or no stress concentrations on the spring around the closed end thereof, fretting fatigue and fretting damage are both minimized.

Figure 11:
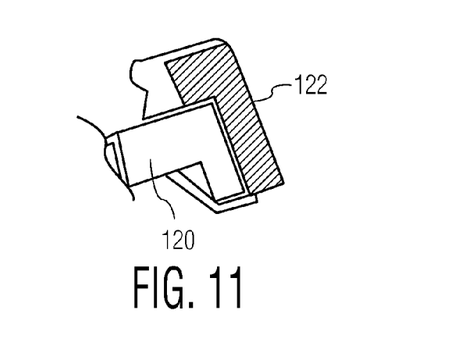
FIG. 11 is a partial view of a closed end V-spring welded to an end assembly.

In yet another embodiment, illustrated in FIG. 11, a closed end V-spring 120 is welded or brazed to the end attachment assemblies 122. In one arrangement, the end of the V-spring will be positioned in a slot in the end attachment assembly and then the two parts are welded together.

Accordingly, a particular solid V-spring arrangement used as part of a driving system for a personal care appliance has been disclosed, useful as, but not limited to, a toothbrush. The V-spring is configured to have end regions, including a closed end arrangement, which allows the ends of the V-spring to be clamped or otherwise attached to end attachment assemblies in a manner which reduces both fretting damage and fretting failure.

While the embodiments disclosed above primarily concern V-spring arrangements, the use of stiffness transition regions on the spring itself to reduce the connection (transition) problem between a "soft" spring and a stiff end attachment member can be made with other spring configurations, including a wire spring and other spring arrangements.

Also, hub attachment assemblies have been disclosed, including spring support portions and clamping blocks, which together operate to clamp end regions of a V-spring. The spring support portions and the clamping members are so configured, and are made of such a material, to reduce stress concentrations in the end regions of the spring which they contact, so as to reduce fretting damage and fretting failure of the V-spring.

Although a preferred embodiment of the invention has been disclosed for purposes of illustration, it should be understood that various changes, modifications and substitutions may be incorporated in the embodiment without departing from the spirit of the invention which is defined by the claims which follow.

The invention claimed is:

1. A combination of a spring member and end assemblies for use in a driving system for a personal care appliance, comprising:
    an elongated solid spring member (18), having a cross-sectional configuration in the form of a V, wherein the spring member has regions (34, 36) at the ends thereof which are large enough to support a contact from an end assembly, the spring member further including a cross-piece (40) extending between the longitudinal edges of the spring member in the end regions thereof; and
    end assemblies for clamping the ends of the spring member, comprising an end block member (64) having a lower support portion (66) on which the end region of the V-spring is positioned, wherein the lower support portion includes an upper peripheral edge (74) which in cross-section is curved to contact an inner surface (67) of the V-spring in an end region thereof, and clamping members (81) which are positioned on top of the V-spring for clamping the end region of the V-spring to the lower support portion of the end block member, the clamping member having a lower surface configuration which fits over the V-spring, the clamping member including a peripheral edge (91), curved in cross-section, which contacts an outer surface of the V-spring substantially in registry with the lower support portion at the inner surface of the V-spring, wherein the physical contact between the lower support portion and the clamping member, respectively, and the V-spring, including the shape of the respective peripheral edges, results in reduced stress concentrations with the V-spring, thereby reducing fretting damage and fretting fatigue.

2. The combination of claim 1, wherein the end regions of the spring member are sufficiently stiff that the transition between the spring action and the end assemblies at the ends thereof occurs within the spring.

3. The combination of claim 1, wherein the personal care appliance is a toothbrush.

4. The combination of claim 1, wherein the lower support portion of the end block member includes a substantially vertical surface (70) which extends outwardly from the body portion, generally curving or angling to a center region 73) and then curving or angling back to the body portion, and wherein the clamping member has surfaces which are similar to or a mirror image of the lower support portion.

5. The combination of claim 1, including a fastener assembly (81) for clamping the clamping member, the V-spring and the lower support portion firmly together.

6. A combination of a spring member and end assemblies for use in a driving system for a personal care appliance, comprising:
an elongated solid spring member (100), having a cross-sectional configuration in the form of a V, wherein the member has regions at the ends thereof which are large enough to support a contact from an end assembly; and
end assemblies (102, 104) for clamping the ends of the spring member, each comprising an end block member having a lower support portion on which an end region of the V-spring is positioned, wherein the lower support portion includes an upper peripheral edge which in cross-section is curved to contact an inner surface of the V-spring in an end region thereof, and clamping members (105) which are positioned on top of the V-spring for clamping the end regions of the V-spring to the lower support portions of the end block members, the clamping members having a lower surface configuration which fits over the V-spring, the clamping members including a peripheral edge, curved in cross-section, which contacts an outer surface of the V-spring substantially in registry with the lower support portion at the inner surface of the V-spring, wherein the physical contact between the lower support portion and the clamping member, respectively, and the V-spring, including the shape of the respective peripheral edges, results in reduced stress concentrations with the V-spring, thereby reducing fretting damage and fretting fatigue.

7. The combination of claim 6, wherein the end regions of the spring member are sufficiently stiff that the transition between the spring action and the end assemblies at the ends thereof occurs within the spring.

8. The combination of claim 6, wherein the personal care appliance is a toothbrush.

9. The combination of claim 6, wherein the lower support portion of the end block member includes a substantially vertical surface (70) which extends outwardly from the body portion, generally curving or angling to a center region 73) and then curving or angling back to the body portion, and wherein the clamping member has surfaces which are similar to or a mirror image of the lower support portion.

10. The combination of claim 6, including a fastener assembly (81) for clamping the clamping member, the V-spring and the lower support portion firmly together.

11. A combination of a spring member and end assemblies for use in a driving system for a personal care appliance, comprising:
an elongated solid spring member (10), having a cross-sectional configuration in the form of a V, wherein the spring member has regions at the ends thereof which are large enough to support a contact from end holding assemblies, the spring member further including a cross-piece extending between the longitudinal edges of the spring member and the end regions thereof; and
end assemblies (112, 114) for holding the ends of the V-spring, comprising an end block member having a triangular slot (116) in one surface thereof for receiving an end region of the V-spring, wherein the slot is sufficiently deep that when the V-spring is secured to the end assembly by an adhesive in the slot, efficient transfer of the torque between the end block member and the V-spring occurs, and wherein the end block is further configured and arranged to minimize relative motion between the block member and the V-spring sufficiently to significantly reduce fretting damage to the spring and to significantly reduce contact stresses and stress concentrations in the end regions of the spring.

12. The combination of claim 11, wherein the end regions are sufficiently stiff that the transition between the spring action and the end assemblies at the ends thereof occurs within the spring.

13. The combination of claim 11, wherein the personal care appliance is a toothbrush.

14. The combination of claim 11, wherein a spring member and end assemblies for use in a driving system for a personal care appliance, comprising:
an elongated solid spring member (120), having a cross-sectional configuration in the form of a V, wherein the spring member has regions at the ends thereof which are large enough to support a contact from an end holding assembly, the spring member further including a cross-piece between the longitudinal edges of the spring member and the end regions thereof, such that the ends of the spring member define a closed loop; and
end assemblies (122) for holding the ends of the V-spring, comprising an end block assembly configured to receive the end regions of the V-spring, wherein the V-spring is welded or brazed to the end block assembly so as to minimize relative motion between the end block member and the V-spring sufficiently to significantly reduce fretting damage to the spring and to significantly reduce contact stresses and stress concentrations in the end regions of the spring.

15. The combination of claim 14, wherein the end regions of the spring member are sufficiently stiff that the transition between the spring action and the end assemblies at the ends thereof occurs within the spring.

16. The combination of claim 14, wherein the personal care appliance is a toothbrush.

* * * * *